(12) United States Patent
Hsu et al.

(10) Patent No.: US 6,855,343 B2
(45) Date of Patent: Feb. 15, 2005

(54) METHOD TO ASCERTAIN THE QUALITY OF HERBS

(75) Inventors: Li-Wei Hsu, Taichung (TW); Su-Chen Chang, Taichung (TW)

(73) Assignee: Advanced Gene Technology, Corp, Taichung (TW)

( * ) Notice: Subject to any disclaimer, the term of this patent is extended or adjusted under 35 U.S.C. 154(b) by 58 days.

(21) Appl. No.: 10/154,208

(22) Filed: May 21, 2002

(65) Prior Publication Data

US 2003/0219498 A1 Nov. 27, 2003

(51) Int. Cl.⁷ .................................................. A61K 35/78
(52) U.S. Cl. ........................ 424/725; 435/174; 435/178
(58) Field of Search ........................... 424/725; 435/174, 435/178; 426/174, 178

(56) References Cited

U.S. PATENT DOCUMENTS 6,156,291 A   12/2000   Pang et al.

*Primary Examiner*—Leon B. Lankford, Jr.
*Assistant Examiner*—Susan D. Coe
(74) *Attorney, Agent, or Firm*—Morrison & Foerster LLP

(57) ABSTRACT

The present invention relates to a novel method useful for fast separation and quick identification of active ingredients in herbs. The separation procedures are efficient without tedious and time-consuming works by using chromatographies or HPLC. The present invention further relates to a method for ascertaining the quality of herbs by applying treated plastic slides on quality control of herbal fractions, based on identification of their biological activities.

39 Claims, 3 Drawing Sheets

SCHEME 1. PREPARATION OF HERB EXTRACT FRACTIONS
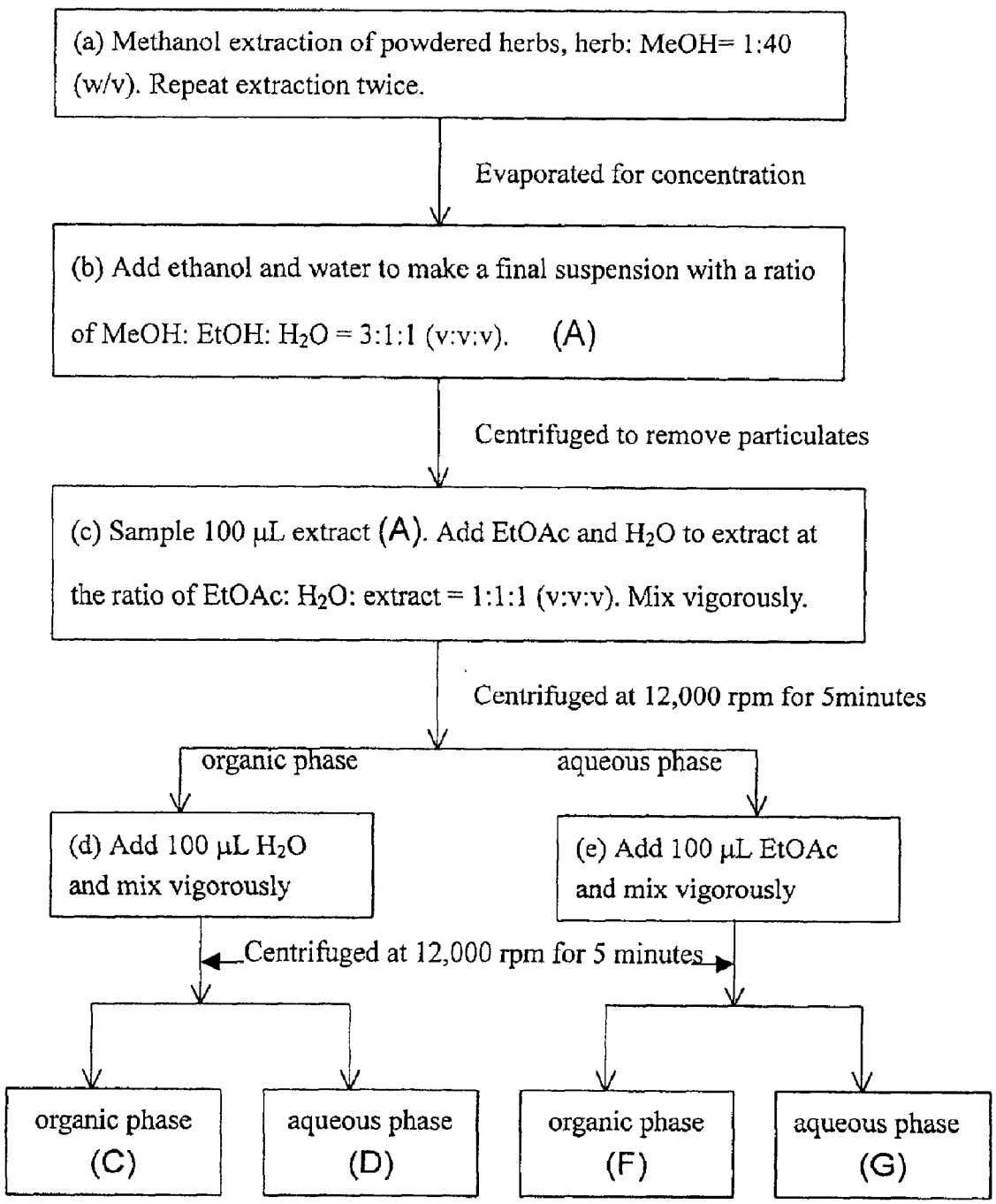

TABLE 1

| | Botanic names of analyzed herbs | Binding activities towards TNFα | | | | | | |
|---|---|---|---|---|---|---|---|---|
| | | A | B | C | D | E | F | G |
| 1 | *Crateva adansonii* DC subsp *formosensis* Jacobs | — | — | — | — | — | — | — |
| 2 | *Machilus japonica* Sieb&Zucc var *kusanoi* (Hayata) | ++ | ++ | + | ++ | ++ | — | + |
| 3 | *Nephrolepis auriculata* (L) Trimen | ++ | ++ | ++ | ++ | ++ | ++ | — |
| 4 | *Dichondra micrantha* Urban | — | — | — | — | — | — | — |
| 5 | *Rorippa indica* (L) Hiern | — | — | — | — | — | — | — |
| 6 | *Ranunculus sceleratus* L | + | + | — | — | — | — | — |
| 7 | *Cleyera japonica* Thunb var *morii* (Yamamoto) Masam | + | + | — | — | — | — | — |
| 8 | *Cayratia japonica* (Thunb) Gagnep | + | + | + | + | + | — | — |
| 9 | *Symplocos chinensis* (Lour) Druce | ++ | ++ | + | ++ | ++ | ++ | ++ |
| 10 | *Amaranthus spinosus* L | + | + | — | + | + | + | — |
| 11 | *Lindera akoensis* Hayata | — | — | — | — | — | — | — |
| 12 | *Morus australis* Poir | — | — | — | — | — | — | — |
| 13 | *Eurya nitida* Korthals | ++ | — | — | + | + | — | — |
| 14 | *Breynia officinalis* Hemsley var *accrescens* (Hayata) MJ Deng & JC Wang | + | + | + | + | + | + | — |
| 15 | *Callicarpa formosana* Rolfe | + | + | + | + | ++ | ++ | + |
| 16 | *Cinnamomum kotoense* Kanehira & Sasaki | + | + | — | + | — | — | — |
| 17 | *Clerodendrum cyrtophyllum* Turcz | — | — | — | — | — | — | — |
| 18 | *Zanthoxylum nitidum (Roxb) DC* | — | — | — | — | — | — | — |
| 19 | *Sarcandra glabra* (Thunb) Nakai | + | + | + | + | + | — | — |
| 20 | *Chamaesyce hirta* (L) Millsp | + | — | — | + | ++ | + | — |
| 21 | *Gonostegia hirta* (Blume) Miq | — | — | — | — | — | — | — |
| 22 | *Ficus erecta* Thunb var *beecheyana* (Hook & Arn) | — | — | — | — | — | — | — |
| 23 | *Machilus obovatifolia* (Hayata) Kanehira & Sasaki | — | — | — | — | — | — | — |
| 24 | *Calocedrus macrolepis* Kurz var *formaosana* (Florin) | ++ | + | + | + | — | — | — |
| 25 | *Urena lobata* L | ++ | ++ | — | ++ | + | + | — |
| 26 | *Rhododendron oldhamii* Maxim | + | + | + | + | — | — | — |
| 27 | *Crateva adansonii* DC subsp *formosensis* Jacobs | — | — | — | — | — | — | — |
| 28 | *Calocedrus macrolepis* Kurz var *formaosana* (Florin) | + | + | + | + | — | + | — |

METHOD TO ASCERTAIN THE QUALITY OF HERBS

TECHNICAL FIELD OF THE INVENTION

The present invention relates to a novel method useful for fast separation and quick identification of active ingredients in herbs. The separation procedure comprised in the method of the present invention is efficient with no need of performing tedious and time-consuming works in comparison with chromatography or HPLC. The present invention further relates to a method for ascertaining the quality of herbs by applying treated plastic slides to the quality control of herbal fractions, based on identification of their biological activities.

BACKGROUND OF THE INVENTION

Herbs have been usually used as a whole plant for medical application for so many years. Herbs are typically ingested as an infusion or tea, or are applied externally as a poultice. It had been found, however, that there is significant variance in the medical effect among individuals of herbs of the same species, when the herbs are treated by the same way.

The ingredients of an herb are typically a mixture of many chemical compounds, and some of the chemical compounds might be biologically active and have a therapeutic effect on human and animals. The ingredients of an herb may vary in their compound species and/or the relative amount thereof, depending upon the genetic information of the individuals of the herb and the natural conditions when the herb grows, such as the geographic region for cultivation, soil composition, water quality, weather conditions including temperature and humidity, sunshine intensity, and growth period.

The effect of herbs for medical application to human and animals is dependent upon the presence of several active compounds and their relative amount contained in the herbs. The higher amount of the active compounds is present in an herb individual, the higher therapeutic effect may be achieved. In the prior art, there is no scientific guideline to detect the presence of desired active ingredients in an herb and their relative amount, even when the herb had already been known to have a specific therapeutic function. The quality of an herb individual having been known to have a therapeutic effect on human and animals is conventionally judged based on just the skilled people's experience in, such as, observing the herbal body shape, color and tissue's texture, smelling its flavor and/or tasting tissue's fluid. There is no teaching in the art to ascertain, by a scientific and systematic way, the quality (i.e. the presence of desired active ingredients and/or their relative amount) of herbs having a therapeutic effect on human and animals.

U.S. Pat. No. 6,156,291 discloses a method of reproducibly extracting a pharmacologically active mixture of chemical components from a plant source, wherein there is an improved quality control of the mixtures of pharmacologically active components.

To solve this problem, based on the finding of the inventor, the present application provides an efficient, scientific and quick method for detecting and ascertaining the presence of active ingredients in the herb individuals, whereby those herb individuals having active ingredients and in turn a desired therapeutic effect could be screened.

SUMMARY OF THE INVENTION

The present application provides a novel method useful for fast separation and quick identification of active ingredients in herbs, comprising the steps of:

(a) extracting the herbs with a solvent to obtain a herbal extract followed by concentrating the herbal extract by evaporation;
(b) mixing the concentrated herbal extract with water and a water-miscible organic solvent followed by removing resultant insoluble particulates to obtain fraction A;
(c) conducting partition extraction of fraction A by mixing fraction A with water and a water-immiscible organic solvent and separating phases to obtain an organic fraction B and an aqueous fraction E;
(d) mixing water with said fraction B and conducting partition extraction to obtain an organic fraction C and an aqueous fraction D;
(e) mixing a water-immiscible organic solvent with said fraction E and conducting partition extraction to obtain an organic fraction F and an aqueous fraction G;
(f) loading a plastic slide which has been pre-treated with each of the resultant fractions A to G; and
(g) conducting hybridization and signal detection for detecting the presence of active ingredients in herbal extract fractions.

The present invention further relates to a method for ascertaining the quality of herbs by applying treated plastic slides for quality control of herbal fractions, based on identification of their biological activities.

The present invention further provides a method for ascertaining the quality of herbs by applying the techniques of biochip for detecting the presence of biologically active ingredient(s) in the herbs capable of specifically binding to tumor necrosis factor-$\alpha$.

BRIEF DESCRIPTION OF THE DRAWING

Scheme 1 shows the procedures of partition extraction according to the preferred embodiment of the invention.

Figure 1:
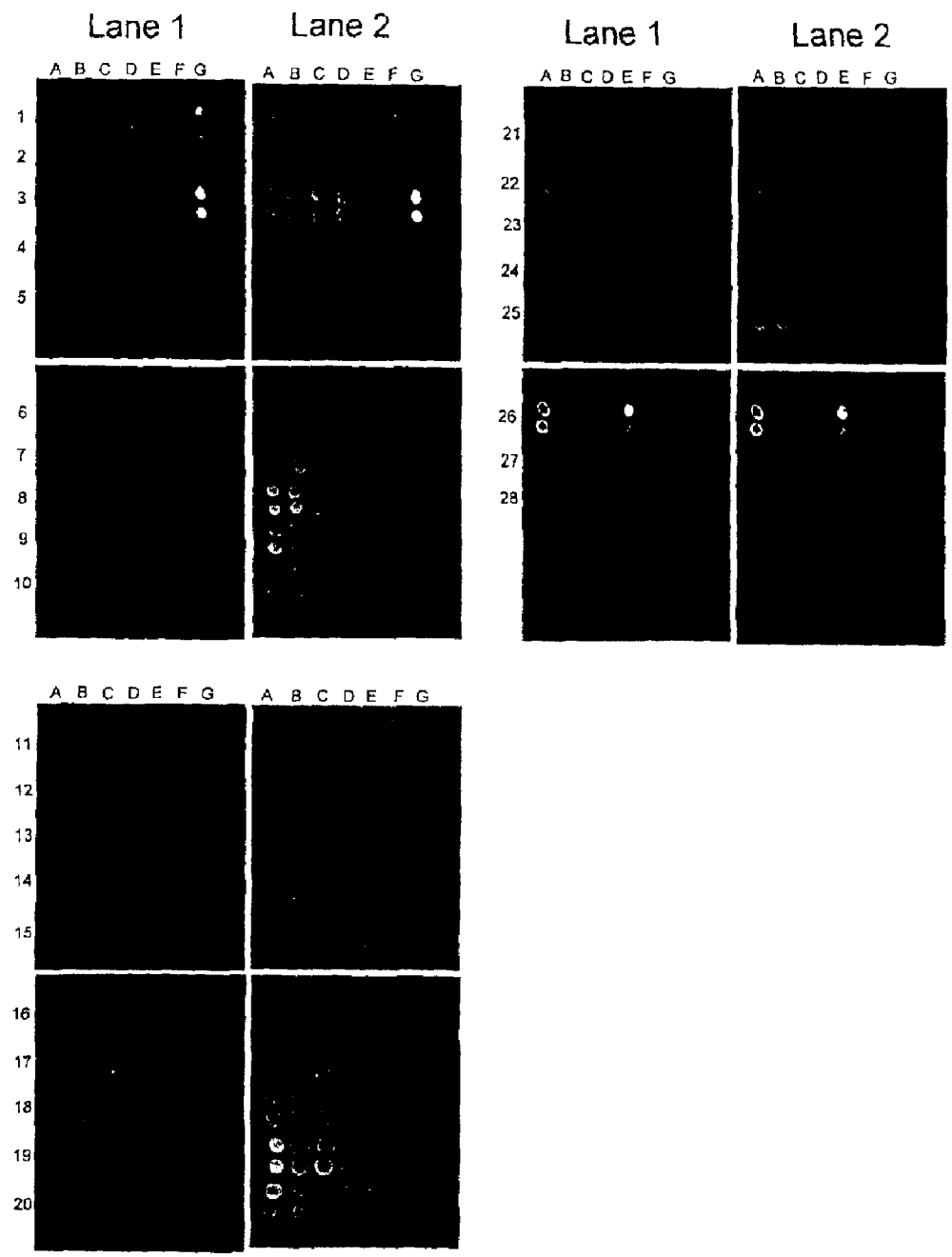
FIG. 1 shows the fluorescent image of the extract fractions A to G obtained according to the invention.

Table 1 shows the binding activity of the extract fractions toward biotinylated TNF$\alpha$ (B-TNF$\alpha$) for each of individual herbs.

DETAILED DESCRIPTION OF THE INVENTION

The present invention provides a novel method useful for fast separation and quick identification of active ingredients in herbs. The separation procedure comprised in the method of the present invention is efficient with no need of performing tedious and time-consuming works in comparison with chromatography or HPLC. The procedure of partition extraction of the herbs according to the invention is illustrated in Scheme 1.

In the method of step (a), the herbs are first ground into fine powders which in turn are extracted with a solvent to obtain herbal extracts. The solvent used in step (a) includes water, alkanols, ethers, esters and a combination thereof. The solvent is preferably alkanols having 1 to 6 carbon atoms, particularly methanol. The ratio of the herbs to solvent is from about 1:30 to about 1:50 (w/v), preferably about 1:40 (w/v). The extraction is conducted at least once, preferably twice. The herbal extracts are then pooled and concentrated by evaporation to obtain a mixture.

In the method of step (b), the resultant concentrated methanol mixture obtained in step (a) is then subjected to a further extraction by vigorously mixing with water and a water-miscible organic solvent in a ratio of about 2–4:0.5–1.5:0.5–1.5 (v:v:v), preferably about 3:1:1 (v:v:v). After centrifugation to remove the insoluble particulates/pellets, a clear supernatant is then obtained as fraction A.

The water-miscible organic solvent used in step (b) is preferably alkanols having 1 to 6 carbon atoms, particularly ethanol.

In the method of step (c), fraction A is partitioned between water and a water-immiscible organic solvent followed by separation to obtain an organic fraction B and an aqueous fraction E. The ratio of fraction A:water:water-immiscible organic solvent is about 0.5–1.5:0.5–1.5:0.5–1.5 (v/v/v), preferably about 1:1:1 (v/v/v). The water-immiscible organic solvent used in step (c) is a carboxylic acid ester having 3 to 10 carbon atoms, preferably ethyl acetate.

In the method of steps (d) and (e), the organic fraction B and organic fraction E are further respectively partitioned between water and a water-immiscible organic solvent followed by separation to obtain an organic fraction C and an aqueous fraction D for fraction B, and an organic fraction F and an aqueous fractions G for fraction E. The partitions in steps (d) and (e) are conducted in a ratio of water to the water-immiscible organic solvent about 0.5–1.5:0.5–1.5 (v/v), preferably about 1:1 (v/v). The organic solvent to be used in steps (d) and (e) is preferably ethyl acetate.

A coated plastic slide which has been pretreated is loaded with the each of resultant fractions A to G in microarray format, which in turn are subjected to hybridization and signal detection under conditions known to the persons skilled in the art.

Each of the herb fractions can contain one herb extract fraction or a mixture of herb extract fractions. The herbs are selected from the group consisting of *Crateva adansonii* DC subsp *formosensis* Jacobs, *Machilus japonica* Sieb&Zucc var *kusanoi* (Hayata), *Nephrolepis auriculata* (L) Trimen, *Dichondra micrantha* Urban, *Rorippa indica* (L) Hiern, *Ranunculus sceleratus* L, *Cleyera japonica* Thunb var *morii* (Yamamoto) Masam, *Cayratia japonica* (Thunb) Gagnep, *Symplocos chinensis* (Lour) Druce, *Amaranthus spinosus* L, *Lindera akoensis* Hayata, *Morus australis* Poir, *Eurya nitida* Korthals, *Breynia officinalis* Hemsley var *accrescens* (Hayata) M J Deng & J C Wang, *Callicarpa formosana* Rolfe, *Cinnamomum kotoense* Kanehira & Sasaki, *Clerodendrum cyrtophyllum* Turcz, *Zanthoxylum nitidum* (Roxb) DC, *Sarcandra glabra* (Thunb) Nakai, *Chamaesyce hirta* (L) Millsp, *Gonostegia hirta* (Blume) Miq, *Ficus erecta* Thunb var *beecheyana* (Hook & Arn), *Machilus obovatifolia* (Hayata) Kanehira & Sasaki, *Calocedrus macrolepis* Kurz var *formaosana* (Florin), *Urena lobata* L, *Rhododendron oldhamii* Maxim, *Calocedrus macrolepis* Kurz var *formaosana* (Florin), and a mixture thereof.

In the present invention, the plastic slide may be made of a homopolymer or copolymer, which is produced by polymerizing one or more monomers selected from the group consisting of ethylene, haloethylene, propylene, halopropylene, acrylate, methacrylate, butadiene, acrylonitrile, norbornene and styrene, wherein a homopolymer of styrene is preferred. The plastic slide may be also made of polycarbonate. The plastic slide used in the present invention is comparable in size to the one conventionally used for a microarrayer and a laser scanner. The advantage of using a plastic slide in the method of the present invention is that there are a variety of chemicals that can be used for treating the surface of a plastic slide, whereby not only macromolecules (such as proteins and DNAs) but also micromolecules (such as metabolites of herbs) can be immobilized on the surface of the plastic slide, in view of the fact that the conventional glass slide is used for immobilizing just macromolecules, such as proteins and DNAs. Further, upon molding, a plastic slide can have a shape as desired and is also effective in cost. The plastic slide can have one or more cavity chambers depending on the desire, cost of manufacture, sensitivity of detection and so on. In an embodiment of the present invention, the plastic slide has two cavity chambers. The samples obtained from fractions of herbs can be gridded into the cavity chambers, and then the cavity chambers can be loaded with a probe(s)-containing solution for conducting hybridization. The depth of the two cavity chambers may be the same or different, and ranges from less than 0.03 mm to up to 0.5 mm. Further, upon molding, two bars may be respectively located at the opposite sides of each chamber for supporting a glass lid, wherein the glass lid is useful for preventing the evaporation or loss of the probe(s)-containing solution, with which the chambers are loaded.

In the pretreatment of the plastic slides and preparation of coated plastic slides, the plastic slides are pretreated with a polyfunctional aldehyde, followed by soaking the plastic slide in a solution of $NH_2$ group(s)-providing precursor, whereby the resultant plastic slides contain active amino groups on their surface. The $NH_2$ group(s)-providing precursor may be organic or inorganic, and may be selected from the group consisting of $NH_4OH$, primary amines, secondary amines and tertiary amines, wherein the aliphatic or aromatic part of the primary amines, secondary amines and tertiary amines may be useful as an additional spacer arm. Among the $NH_2$ group(s)-providing precursors, $NH_4OH$ directly providing free $NH_2$ group is preferred.

In the present invention, the coating on the plastic slides comprises polyfunctional molecules, e.g. polyfunctional epoxides, as a spacer. The polyfunctional epoxides act for linking the ingredients contained in herbs to the pretreated plastic slides. The active epoxy groups on one end of the polyfunctional epoxides react with the amino groups on the surface of the pretreated plastic slides, while active epoxy groups on the other end of the polyfunctional epoxides react with or absorb the ingredients contained in the herbs. In particular, those ingredients contained in the herbs that contain free hydroxyl, sulfhydryl or amino groups can form a covalent bond with the active epoxy groups on the polyfunctional epoxides, and consequently are attached onto the coated plastic slides. The polyfunctional epoxides preferably contain a long chemical chain of 6 to 24 carbon atoms, whereby the ingredients of herbs would not directly bind to the pretreated plastic slide. In the method of the present invention, the binding of each of sample spots to the coated plastic slide is persistent, even after stringent stripping. In the present invention, not only macromolecules (such as proteins and DNAs) but also small molecules (such as metabolites of herbs) can be immobilized in a homogeneous or heterogeneous manner on the surface of the coated plastic slides.

In the step of loading the coated plastic slides with fraction samples of the herb extracts in microarray format, the fraction samples of herb extracts are spotted and immobilized on the coated plastic slide in a gridded area in microarrays with a microarrayer by applying the high-density gridding technology, wherein each of sample spots may contain homogeneous or heterogeneous ingredients of herbs. In the method of the present invention, the integrating miniaturization technique can be used for increasing the density of samples gridded on the coated plastic slides.

In the method of the present invention, the detection of the presence of biologically active desired ingredient(s) in herbs for ascertaining the quality of the herbs is based on a target-directed strategy, which comprises loading the chambers of the coated plastic slides with a labeled probe(s)-containing solution for conducting hybridization (wherein each of the chambers may be covered by a glass lid for preventing the evaporation of the labeled probe(s)-containing solution), and imaging and identifying the sample spots that react with or bind to the labeled probe with an apparatus, e.g. a laser scanner. The probes used in the method of the present invention may be homogeneous or heterogeneous, known targets based on a defined molecular mechanism, which may be, for example, small molecules, competitive ligands, or antibodies against, for example, the selected cells, receptors, enzymes, or proteins. The label within the probes may be a dye or a radioactive material.

In a preferred embodiment, the present invention provides a method for ascertaining the quality of herbs by applying the techniques of biochip for detecting the presence of biologically active ingredient(s) in the herbs capable of specifically binding to a probe, i.e., the tumor necrosis factor-α (TNF-α). In particular, for use as a probe for conducting hybridization in the method of the present invention, TNF-α, is labeled with biotin and strepavidin is labeled with Cy3. In accordance with the method of the present invention, if a signal indicating the binding of the ingredient(s) in a sample spot on the treated plastic slides to the biotinylated TNF-α is observed, there should be at least one candidate in the ingredients of the sample spot that exhibits a biological activity toward TNF-α. The candidate may be useful in the treatment of autoimmune diseases, such as rheumatoid arthritis.

Without further elaboration, it is believed that persons with ordinary skill in the art can, based on the description herein, utilize parts or the whole procedures to its full extent. The following Examples are to be construed as merely illustrative, and not limitative of the disclosure of the present invention in any way.

EXAMPLES

Example 1

Partition of Herbal Extracts

The procedures of partition of herb extracts are presented as in Scheme 1. After the collected herbs were washed and dried, methanol was added to 50 g of herb (40/1, v/w). The ingredients in the herbs are extracted by blending the mixture and pooling the supernatant obtained by subjecting resultant methanolic extract to centrifugation at 8000 rmp at 4° C. for 30 min. Extraction was repeated twice with the same procedures as mentioned above. The pooled extract was concentrated to a final volume of about 30 mL on a rotatory evaporator (Heidolph, Laborota 4000). To the concentrated extract 10 mL of ethanol and 10 mL of $H_2O$ were added, and then the mixture was vigorously mixed on Vortex (Heidolph, Redax top) for 2 minutes. The insoluble particulates/pellets were then removed by centrifugation at 12,000 rpm at 4° C. for 5 minutes. A clear supernatant solution was then obtained as fraction A.

An aliquot (100 μL) of fraction A was transferred into a 0.5-mL eppendorf tube, and then to each of 100 μL EtOAc and 100 μL $H_2O$ were added. The mixture was vigorously mixed on Votex, followed by centrifugation at 12,000 rpm at 4° C. for 5 minutes. After settling had taken place, the organic phase (fraction B) and aqueous phase (fraction E) were separated and in turn placed in two 0.5-mL eppendorf tubes. Further partition was performed by adding 100 μL $H_2O$ to the tube containing the organic phase and adding 100 μL EtOAc to the other tube containing the aqueous phase, followed by vigorously mixing each of the tubes on Votex. Each of the two-phase mixtures obtained were centrifuged at 12,000 rpm at 4° C. for 5 minutes, followed by separation of the organic and aqueous phases for both samples to obtain four respective fractions, labeled as fractions C, D, F and G, as indicated in Scheme 1.

Example 2

Pretreatment of the Plastic Slides

Molded plastic slides were made of a polymer of styrene and comprised two cavity chambers. The molded plastic slide was comparable in size with the regular glass slide used for microscope or laser scanner, wherein the depth of each of the cavity chambers is 0.05 mm.

The molded plastic slides were first immersed in an aqueous 0.4% glutaraldehyde solution (pH 5.0) for 4 hours at room temperature, followed by washing with excessive water and then soaking in 3 M aqueous $NH_4OH$ (pH 11.0) at 60° C. for 4 hours. The resultant plastic slides were then treated with 100 mM of 1,4-butanediol diglycidyl ether (pH 11.0) at 37° C. overnight. The plastic slides obtained were washed with 0.1 M aqueous $NaHCO_3$ solution (pH 8.0) once and double-distilled water four times, followed by stored in double-distilled water at 4° C. The resultant slides were dried in a safety cabinet at room temperature prior to use.

Example 3

Loading of Treated Plastic Slides with Herb Fractions

All of the fractions A to G obtained in Example 1 were dried on SpeedVac (Savant) and then redissolved in 50 μL of 50 mM carbonate buffer (pH 9.5) containing 30% DMSO. Each of the partitioned fractions of herbs was manually spotted on the caves of the treated plastic slides obtained in Example 2 in duplicates. The volume of each spot is 0.1~0.2 μL. The spotted plastic slides were dried at 37° C. for 30 minutes. The slides obtained were then immersed in an excessive amount of 1 M aqueous ethanolamine (pH 8.0) and then incubated at 37° C. with gentle agitation for 2 hours. The slides were washed three times with a TBST buffer solution containing 50 mM Tris-HCl, pH 7.3, and 0.15 M NaCl including 0.05% Tween 20, followed by washing with excessive double-distilled water three times. The slides were then allowed to stand to dryness at 37° C. for 5 minutes. The herb-treated slides obtained were ready to use for hybridization or can be sealed under vacuum and stored at 4° C. for a long term. The slides were prescreened using a laser scanner (GenePix 4000, AXON), prior to the addition of the fluorescence labeled probe for hybridization.

Example 4

Biotinylation of Tumor Necrosis Factor Alpha (TNFα)

Biotinylation of TNFα protein was performed by using biotinamidocaproate N-hydroxysuccinimide ester (BACHSE, Sigma B-2643). A solution of BACHSE in dimethyl sulfoxide (DMSO) (5 mg/mL) was prepared. The resultant BACHSE solution was added to the TNFα solution at a ratio of 1:40 (w/w). The reaction was allowed to proceed at room temperature for 30 minutes with occasional agitation. The reaction mixture was then dialyzed against double-distilled water at 4° C. for 1 hour, followed by dialysis against the TBST buffer for 16–18 hours during which the TBST buffer was refreshed twice. The degree of biotinylation of TNFα protein was tested in a 15% SDS-PAGE immunoblotting experiment with avidin-alkaline phosphatase chemically overlying the biotin of the biotinylated TNFα under the protocol conventionally used in the art. The biotinylated TNFα (B-TNFα) was then stored in a glass vial at 4° C. prior to use.

Example 5

Labeling of Strapavidin with Fluorophore

Cy3-strapavidin (SA) was prepared by labeling strapavidin with FluoriLink™Cy3™ bifunctional reactive dye (Amersham) according to the manufacturer's recommended protocol. The uncoupled fluororesent dye was removed by gel filtration chromatography on a Bio-Gel P2 cloumn (0.5 cm×10 cm) (Bio-Rad) previously equilibrated in a TBST buffer. The final concentration of Cy3-labeled strapavidin was estimated to be 0.5 mg/mL by measuring optical density at 280 nm ($OD_{280}$) using a UV spectrophotometer.

Example 6

Hybridization of Herb-Treated Slides

Each of the cavity chambers of the herb-treated plastic slides obtained in Example 3 was respectively covered with a 22×22 mm cover glass. A working solution was prepared by diluting the B-TNFα obtained in Example 4 with the TBST buffer to a concentration of 0.5 μg/mL. 20~25 μL of the B-TNFα solution obtained was slowly infused into each of the cavity chambers of the herb-treated plastic slides. The slides were incubated at room temperature for 2 hr, and then rinsed with the TBST buffer, followed by gently washing with an excess of the TBST buffer three times and double-distilled water four times. The slides were then dried at 37° C. for 5 minutes. A fluorescent reagent was prepared by diluting the stock Cy3-SA solution obtained in Example 5 with the TBST buffer to a final concentration of 0.5 μg/mL. 20~25 μL of the fluorescent reagent was slowly infused into each of the treated plastic slides containing B-TNFα. The slides obtained were incubated at room temperature for 2 hr or at 4° C. overnight. The slides were gently washed with excessive TBST buffer three times and double-distilled water four times, and then dried at 37° C. for 5 minutes. The slides obtained were examined by scanning at 650 nm using GenePix 4000A slide scanner (Axon Instruments). The images of the fluorescent spots were analyzed using Gene-Pix 3.0 Software. The results were shown in FIG. 1.

Results

Each of the herbal extracts is prepared according to the standard procedures as shown by flow chart in Scheme 1. The preliminary crude extract is referred to as fraction A. Then the fraction A obtained from each of the herbs is individually subjected to partial fractionation into six pools (referred to as fractions B to G). 27 herbs to be studied are showed in Table 1 as their Latin name, in which the 27nd herb was identical to the first herb as *Crateva adansonii* DC *subsp formosensis* Jacobs, except that the concentration of the 27nd herb is twice that of the first herb. FIG. 1 shows the images obtained by scanning the slides prior to (Lane 1) and after (Lane 2) the hybridization process. The numerical marks 1 to 28 in FIG. 1 refer to the numberings of the herbs shown in Table 1. The alphabets A to G are corresponding to the individual extract fractions obtained according to the procedures showed in Scheme 1. Each of the extract fractions is prepared from the corresponding herb sample in duplicate.

The images shown in Lane 1 demonstrate that most of the herbal extract fractions carry endogenous fluorophores which show endogenous red fluorescent color under excitation at wavelength 650 nm. The green fluorescent spots showed in Lane 2 of FIG. 1 indicate the binding of Cy3-labled B-TNFα to the herbal extract fraction. The yellowish fluorescent spots shown in Lane 2 of FIG. 1 may be interpreted as the mixing effect of the endogenous red florescence of the herbal extract fraction and the green fluorescence of the bound Cy3-labled B-TNFα. The binding activity of the herbal extract fractions toward B-TNFα for each of individual herbs is shown and summarized in Table 1. The results in Table 1 indicate that 17 out of 27 herbs containing ingredients, in various extract fractions, possess binding activities towards TNFα. The activities were classified as ++, +, or − according to the ratio (R) of the intensity of fluorescence at 650 nm/570 nm. R≧1 is defined as "−"; 0.6<R<1.0 is defined as "+"; and R≦0.6 is defined as "++".

What is claimed is:

1. A method for determining the presence or absence of an ingredient of interest in an herb or a multiplicity of herbs that specifically binds to a probe, comprising the steps of:
    (a) extracting the herb or a multiplicity of herbs with a solvent to obtain an herbal extract followed by concentrating the herbal extract by evaporation;
    (b) mixing the concentrated herbal extract with water and a water-miscible organic solvent followed by removing resultant insoluble particulates to obtain fraction A;
    (c) retaining a first portion of fraction A and mixing a second portion of fraction A with water and a water-immiscible organic solvent and separating phases to obtain an organic fraction B and an aqueous fraction E;
    (d) retaining a first portion of fraction B and mixing water with a second portion of fraction B and conducting partition extraction to obtain an organic fraction C and an aqueous fraction D;
    (e) retaining a first: portion of fraction E and mixing a water-immiscible organic solvent with a second portion of fraction E and conducting partition extraction to obtain an organic fraction F and an aqueous fraction G;
    (f) loading at separate locations on a plastic slide at least a portion of each of fractions A to G; and
    (g) contacting said slide with said probe and detecting any binding of said probe, thereby detecting the presence or absence of an ingredient that specifically binds said probe in said herbal extract fractions.

2. The method ha claimed in claim 1, wherein in step (a), the ratio of the herb to the solvent is from about 1:30 to about 1:50 on a weight:volume basis.

3. The method as claimed in claim 2, wherein in step (a), the ratio of the herb to the solvent is about 1:40 on a weight:volume basis.

4. The method as claimed in claim 1, wherein the solvent in step (a) is selected from the group consisting of water, an organic solvent and a combination thereof.

5. The method as claimed in claim 4, wherein the solvent in step (a) is a polar organic solvent.

6. The method as claimed in claim 5, wherein the solvent in step (a) is an alkanol.

7. The method as claimed in claim 6, wherein the solvent in step (a) is an alkanol having 1 to 6 carbon atoms.

8. The method as claimed in claim 7, wherein the solvent in step (a) is methanol.

9. The method as claimed in claim 1, wherein the extraction in step (b) comprises mixing the herbal extract obtained in step (a) with water and a water-miscible organic solvent in a ratio of about 2–4:0.5–1.5:0.5–1.5 on a volume:volume:volume basis herbal extract: water: water-miscible organic solvent.

10. The method as claimed in claim 9, wherein the extraction in step (b) comprises mixing the herbal extract obtained in step (a) with water and a water-miscible organic solvent in a ratio of about 3:1:1 on a volume:volume:volume basis herbal extract: water: water-miscible organic solvent.

11. The method as claimed in claim 10, wherein the insoluble particulates are removed by centrifugation.

12. The method as claimed in claim 10, wherein to water-miscible organic solvent used in step (b) is an alkanol solvent having 1 to 6 carbon atoms.

13. The method as claimed in claim 12, wherein the water-miscible organic solvent is ethanol.

14. The method as claimed in claim 1, wherein the partition extraction in step (c) comprises mixing the second portion of fraction A with water and a water-immiscible organic solvent in a ratio of about 0.5–1.5:0.5–1.5:0.5–1.5 on a volume:volmne:volume basis fraction A: water: a water-immiscible organic solvent.

15. The method as claimed in claim 14, wherein the partition extraction in step (a) comprises mixing the second portion of fraction A with water and a water-immiscible organic solvent in a ratio of about 1:1:1 on a volume:volume:volume basis fraction A: water: water-immiscible organic solvent.

16. The method as claimed in claim 14, wherein the water-immiscible organic solvent is a carboxylic acid ester having 3 to 10 carbon atoms.

17. The method as claimed in claim 16, wherein the water-immiscible organic solvent is ethyl acetate.

18. The method as claimed in claim 1, wherein the mixing step in step (d) comprises mixing the second portion of fraction B with water in a ratio of about 0.5–1.5:0.5–1.5 on a volume:volume basis fraction B to water.

19. The method as claimed in claim 18, wherein the mixing step in step (d) comprises mixing the second portion of fraction B with water in a ratio of about 1:1 on a volume:volume basis fraction B to water.

20. The method as claimed in claim 1, wherein the mixing step in step (e) comprises mixing a water-immiscible organic solvent with the second portion of fraction E in a ratio of about 0.5–1.5:0.5–1.5 on a volume:volume basis water-immiscible organic solvent to the second portion of fraction E.

21. The method as claimed in claim 20, wherein the mixing step in step (e) comprises mixing a water-immiscible organic solvent with the second portion of fraction E in a ratio of about 1:1 on a volume:volume basis water-immiscible organic solvent to the second portion of fraction E.

22. The method as claimed in claim 20, wherein the water-immiscible organic solvent used in step (e) is ethyl acetate.

23. The method as claimed in claim 1, wherein the material of the plastic slide is a polycarbonate, or a homopolymer or copolymer made atone or more monomers selected from the coup consisting of ethylene, haloethylene, propylene, halopropylene; acrylate, methacrylate, butadiene, acrylonitrile, norbornene and styrene.

24. The method as claimed in claim 23, wherein the plastic slide is made of a polymer of styrene.

25. The method as claimed in claim 1, wherein the plastic slide is pre-treated with a polyfunctional aldehyde, followed by soaking in a solution of $NH_2$ groups-providing and then coated with one or more polyfunctional molecules.

26. The method as claimed in claim 25, wherein the polyfunctional aldehyde is glutaldehyde.

27. The method as claimed in claim 25, wherein the $NH_2$ groups-providing precursor is $NH_4OH$.

28. The method as claimed in claim 25, wherein the polyfunctional molecule is a polyfunctional epoxide containing at least one epoxide group at each of its ends.

29. The method as claimed in claim 28, wherein the epoxide groups at the ends of the polyfunctional epoxide react with the amino groups on the surface of the pretreated plastic slides.

30. The method as claimed in claim 28, wherein the epoxide groups at the ends of the polyfunctional epoxide react with the free hydroxy, sulfhydryl or amino groups of the ingredients contained in the herb or mixture.

31. The method as claimed in claim 28, wherein the polyfunctional epoxide contains a long chemical chain of 6 to 24 carbon atoms.

32. The method as claimed in claim 1, wherein the herb is selected from the group consisting of *Crateva adansonii subsp formosensis, Machilus japonica var kusanoi, Nephrolepis auriculata, Dichondra micrantha, Rorippa indica, Ramunculus sceleratus, Cleycra japonica var morii, Cayratia japonica, Symplocos chinensis, Amaranthus spinosus, Lindera akoensis, Morus australis, Eurya nitida, Breynia officinalis var acerescens, Callicarpa formosana, Cinnamomum kotoense, Clerodendrum cyrtophyllum, Zanthoxylum nitidum (Roxb), Sarcandra glabra, Chamaesyce hirta, Gonostegia hirta, Ficus erecta var beecheyana, Machilus obovatifolia, Calocedrus macrolepis var formaosana, Urena lobata, Rhododendron oldhamii, Calocedrus macrolepis var formaosana*, and mixtures of two or more of the foregoing.

33. The method as claimed in claim 1, wherein said probe is labled.

34. The method as claimed in claim 33, wherein the label is a dye or a radioactive material.

35. A method for visualizing each of a multiplicity of fractions displayed on a surface, wherein said fractions have been obtained by a series of partition extraction steps performed on an extract of said herb multiplicity of herbs, wherein said partition extraction steps performed comprise:

(a) extracting the herb multiplicity of herbs with a solvent to obtain an herbal extract followed by concentrating the herbal extract by evaporation;

(b) mixing the concentrated herbal extract with water and a water-miscible organic solvent followed by removing resultant insoluble particulates to obtain fraction A;

(c) retaining a first portion of fraction A and mixing a second portion of fraction A with water and a water-immiscible organic solvent and separating phases to obtain an organic fraction B and at aqueous fraction B;

(d) retaining a first portion of fraction B and mixing water with a second portion of fraction B and conducting partition extraction to obtain an organic fraction C and an aqueous fraction D;

(e) retaining a first portion of fraction E and mixing a water-immiscible organic solvent with a second portion of fraction B and conducting partition extraction to obtain an organic fraction F and an aqueous fraction G and (f) loadings plastic slide with at least a portion of each of fractions A to G.

36. The method of claim 1 wherein said probe is tumor necrosis factor α(TNFα).

37. The method of claim 36 wherein said TNFα is labeled.

38. The method of claim 37 wherein said label is a dye or radioactive material.

39. The method as claimed in claim 36, wherein the herb or mixture one ingredient that can specifically bind to tumor necrosis factor-α(TNF-α).

* * * * *